United States Patent [19]

Venderjagt

[11] 3,934,463

[45] Jan. 27, 1976

[54] HARDNESS TESTER

[76] Inventor: Adrian Dean Venderjagt, 4075 State St., Bridgeport, Mich. 48722

[22] Filed: Feb. 28, 1974

[21] Appl. No.: 446,967

[52] U.S. Cl. ................................................. 73/81
[51] Int. Cl.² ........................................... G01N 3/42
[58] Field of Search ................................. 73/81, 94

[56] References Cited
UNITED STATES PATENTS

| | | | |
|---|---|---|---|
| 1,192,670 | 7/1916 | Moore et al. | 73/81 |
| 1,768,512 | 6/1930 | Leeuw | 73/81 |
| 3,123,997 | 3/1964 | Cosner | 73/81 |
| 3,296,857 | 1/1967 | Kaczeus | 73/81 X |
| 3,786,676 | 1/1974 | Korolyshun et al. | 73/94 |

Primary Examiner—Charles A. Ruehl
Attorney, Agent, or Firm—John J. Swartz

[57] ABSTRACT

Hardness testing apparatus including a workpiece penetrator, a stop for interrupting movement of the penetrator after it has penetrated the workpiece to a predetermined depth, and mechanism for individually measuring the load on the penetrator when it has penetrated the workpiece to the predetermined depth.

19 Claims, 8 Drawing Figures

HARDNESS TESTER

BACKGROUND OF THE INVENTION

This invention relates to a hardness tester and more particularly to a constant depression, variable force hardness tester.

Prior hardness testing devices generally comprise constant force, variable depression, indentation type hardness testers. Such devices rely on the principle that the force required to make a given depression varies directly with the hardness of the specimen. Such testing devices employ a spherical indenter of known diameter which bears against the workpiece to be tested under a specified load, to form an impression or indentation in the surface of the test piece. The hardness of the test piece is directly proportional to the depth of the indentation. It is difficult to accurately measure the penetration depth and thus the hardness measurements are frequently inaccurate.

One such prior art tester is known as the Brinell type tester and measures the depression after a spherical indenter ball has been removed from the specimen. Thus, elastic recovery of the material after removal of the indenter in this type of tester is another factor which adds to the measuring error. The indentations in the various specimens are geometrically dissimilar and this also adds to the measuring error. In addition, if lighter loads are used to provide a depression diameter which is less than 25% of the diameter of the indenting spherical ball, the depression diameter is quite shallow and is difficult to accurately measure. To form a depression diameter which is greater than 50% of the indenter ball diameter, the material passes so far up on the penetrating ball that minor changes in the hardness can no longer be interpreted accurately. The Brinell method is slow and the Brinell apparatus is cumbersome to operate. All of the established devices are slow and difficult to automate.

Another factor which must be considered in measuring hardness with the prior art tester is "skin effect." Due to different cooling rates, temperatures, etc., the "skin" of the material generally has a different hardness than the underlying portion of the material. Moreover, the outer surface of a cast workpiece is generally uneven or irregular due to different cooling rates and temperatures of the casting. If the material being tested is very hard and the skin relatively soft, the penetrating ball will easily penetrate the soft skin layer, but will make a very little indentation in the underlying hard material. If the thickness of the skin layer constitutes a substantial portion of the overall depression, the instrument will erroneously read "soft."

Prior to conducting a hardness test the prior art testing devices the surface or skin material must generally be removed by grinding, for example, and this further slows the prior art testing procedures.

Another prior art hardness testing device utilizes an electrical control circuit having an electrical circuit path which includes a portion of the workpiece. This type of testing apparatus will test only electrically conductive workpieces.

An object of the present invention is to provide a hardness tester which will measure hardness with improved accuracy.

Another object of the present invention is to provide hardness testing apparatus which will enable the rate of testing to be increased.

Another object of the present invention is to provide a hardness testing apparatus for accurately measuring the hardness of a workpiece having an irregular surface.

It is another object of the present invention to provide hardness testing apparatus which will measure hardness by measuring the force or load required to provide a predetermined indentation in the material.

Another object of the present invention is to provide a hardness testing machine of the type described which provides a geometrically similar, constant-depth depression in various materials with variable loads being exerted on the penetrator.

Still another object of the present invention is to provide hardness testing apparatus which will measure the hardness of electrically conductive and non-conductive workpieces.

A further object of the present invention is to provide apparatus of the type described incorporating a stop which will positively interrupt movement of the penetrator into the test specimen after it has penetrated the workpiece to a predetermined depth.

Yet another object of the present invention is to provide hardness testing apparatus of the type described which will individually determine the load on the indenter when it has penetrated the test piece to a predetermined depth.

Another object of the present invention is to provide hardness testing apparatus of the type described which will individually determine the loads exerted on the workpiece penetrator and the stop.

Another object of the present invention is to provide hardness testing apparatus of the type described which will indicate whether the hardness for a test specimen falls within a predetermined range only after the load on the stop reaches a predetermined level.

Other objects and advantages of the present invention will become apparent to those of ordinary skill in the art as the description thereof proceeds.

SUMMARY OF THE INVENTION

A hardness tester, including a workpiece penetrator, a stop for interrupting movement of the penetrator into the workpiece, and mechanism for directly, individually measuring the force required to penetrate the workpiece.

The present invention may more readily be understood by reference to the accompanying drawings, in which.

Figure 3:
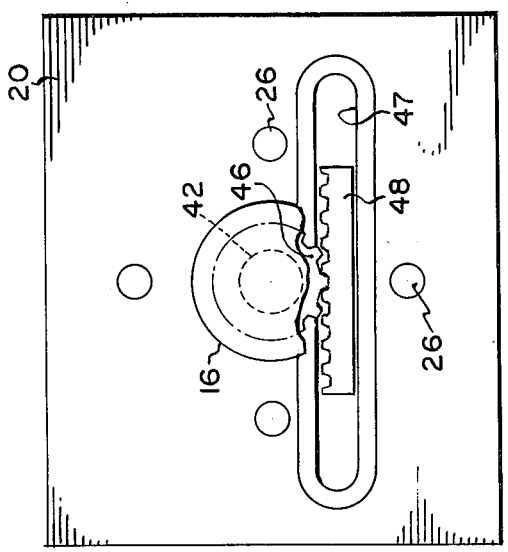
FIG. 3 is a top plan view of the apparatus illustrated in FIG. 2.

Apparatus constructed according to the present invention is adapted for use in a hydraulically operated press or compacting machine, generally designed 10, including a frame F mounting a horizontally disposed work table 12 which supports a workpiece or specimen W to be tested. The frame F includes vertical ways 15 which mount a carriage 13 for vertical movement. A double acting, solenoid actuated, fluid pressure operated cylinder 14 is mounted on the frame F and includes a piston rod 14' connected to the carriage 13 for vertically moving the carriage 13 toward and away from a workpiece W. Mounted on the front of the carriage 13 is a support rod 16 having test apparatus generally designated 18, mounted thereon.

Figure 2:
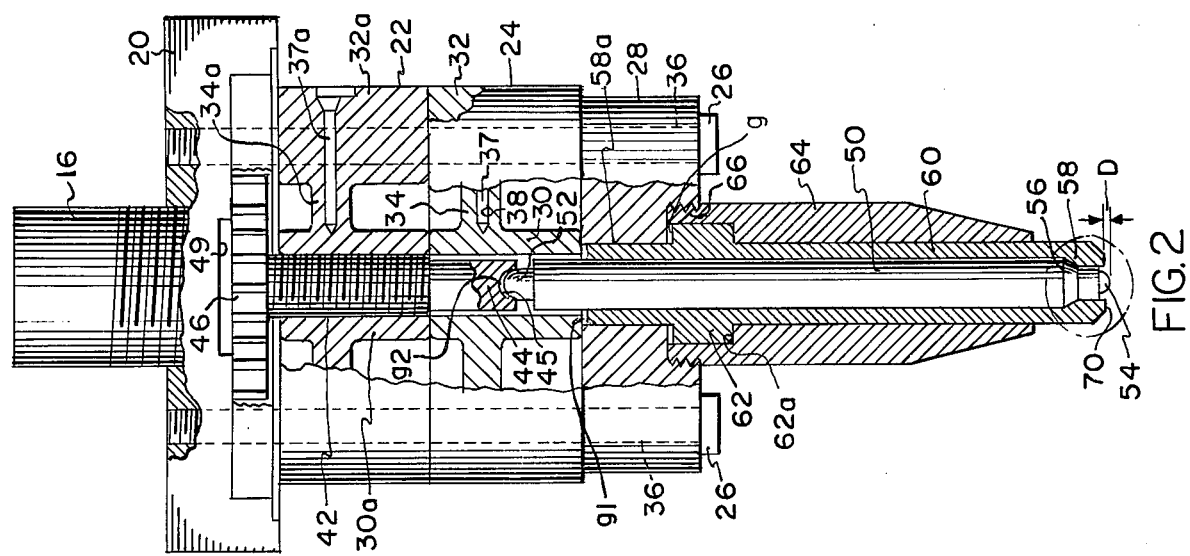
FIG. 2 is an enlarged, partly sectional, side elevational view of apparatus constructed according to the present invention.

Turning now to FIG. 2, the test apparatus 18 includes a carrier, generally designated 20, threaded on the lower end of the support rod 16. A pair of load cells, generally designated 22 and 24, are clamped to the carrier 20 by an underlying guide holder 28 and a plurality of vertically extending bolts 26 threaded in the carrier 20. Load cells of the type sold under the trademark STRAINSERT, manufactured under U.S. Pat. No. 3,365,689, which is incorporated herein by reference, have been found to be suitable for this purpose.

The load cells 22 and 24 are identical and the load cell 24, for example, comprises a body member of metal or other suitable material, having a generally overall flat, circular configuration including a hub portion 30, a rim portion 32, and an intermediate reduced axial thickness web portion 34. A plurality of circumferentially spaced holes 36 in the rim 34 receive the vertical bolts 26. A series of circumferentially spaced, radially extending holes 38 are provided in the rib portion 34 for receiving strain gauges 37 as described in the referenced patent. The load cell 22 is identical to the load cell 24, and identical parts will be identified with identical reference characters followed by the letter a.

Threaded into the hub 30a of the load cell 22 is a load screw 42 having a reduced diameter stub shaft terminal portion 44 provided with a semi-spherical recess or socket 45 for a purpose to be immediately described. The upper end of the screw 42 is provided with an integral gear 46 which is engaged by a reciprocal rack 48 (FIG. 3) slidably received in a slot 47 provided in the carrier 20. The recess 45 is provided for enabling the load screw 42 to be vertically adjusted as it is turned for a purpose to become immediately apparent.

Figure 3A:
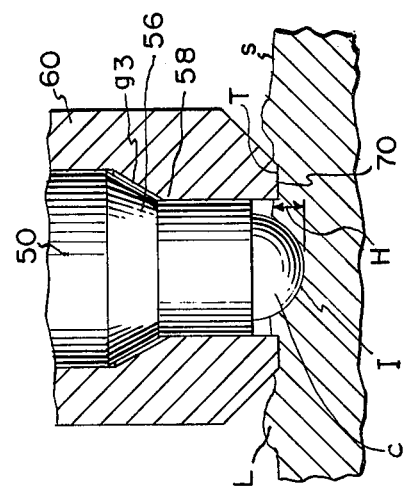
FIG. 3A is a further enlarged view of the tip of the specimen penetrator which is encircled in chain lines in FIG. 2.

Apparatus is provided for penetrating the workpiece and comprises a hardness punch or vertically extending penetrator rod 50 having a reduced diameter, semi-spherical upper end portion 52 received by the semi-spherical socket 45 in the lower end or the threaded screw 42. A slight gap $g2$ is provided between the upper end 52 and the socket 45 to permit the rod 50 to be "jiggled" as will be described more fully hereinafter. A spherical, carbide indenter or penetrator ball 54, having a diameter of 0.125–0.187 inches, for example, is partially received in a complementally shaped recess provided in the lower end of the penetrator rod 50. The penetrator ball 54 is fixed to the penetrator rod 50 by any suitable means such as silver brazing so that the center of gravity $c$ of the ball 54 is disposed a substantial distance below the lowermost end of the penetrator rod 50. This will permit more than 50% of the ball to be used to create an impression I (FIG. 3A). When the carriage 13 is moved downwardly, the penetrator ball 54 is moved downwardly into penetrating engagement with the workpiece W to form an indentation I.

To measure harness consistently and accurately, it is important that the penetrator ball 54 consistently penetrate the specimens W to substantially the same effective depth. For this purpose, a tubular stop member, generally designated 60, is provided to engage the specimen W and positively interrupt movement of the penetrator ball 54 toward the workpiece W. The tubular stop member 60 is received for free vertical movement in a tubular guide member 64 which is threaded at its upper end 66 in the guide holder 28. An annular flange 63 on the tubular stop member is supported by a shoulder 62a on the guide holder 28. The penetrator rod 50 is received by said tubular stop member 60 for free vertical movement therein. The lower end 56 of the penetrator rod 50 is of reduced diameter and is vertically supported by an internal shoulder 58 at the lower end of the stop member 60. The enlarged diameter flange portion 62 and the upper end 58a of the tubular stop member 60 are separated from the guide holder 28 and the load cell hub 30 by vertical gaps $g$ and $g1$, respectively, when the tubular stop member 60 is not engaged with a workpiece W, as illustrated in FIG. 2. The gaps $g$ and $g1$ permit the operator to vertically jiggle the tubular stop member 60 in the holder or tubular guide member 64 to insure that it is freely movable. If material becomes wedged between the tubular guide member or holder 64 and the tubular stop member 60, the tubular stop member 60 will not be freely movable and inaccurate measurements will result. When the tubular stop member 60 bears against a workpiece W, as illustrated in FIG. 3A, the upper end 58a will move upwardly to bear against the load cell hub 30 and close the gap $g1$. The gap $g$ is slightly greater than the gap $g1$ so that the enlarged diameter portion 62 will close the gap $g$ and bear against the guide holder 28 a short time after the gap $g1$ is closed and after the web 34 has been deformed a predetermined amount. Any further vertical loading is transmitted to the support rod 16 via the stop member flange 62, the guide holder 28, the load cell rims 32, and the carrier 20. This will prevent permanent deformation of the web 34 which might otherwise result when a very hard specimen is tested.

If the skin $s$ is very soft, the tubular stop member 60 will displace at least some of the skin material and will not interrupt movement of the penetrator ball 54 until the tubular stop member 60 bears against the underlying material with a sufficient predetermined force which is measured in a manner to be later described. The flat end surface 70 of the tubular stop will also, when penetrating the skin $s$ to the depth T, flatten or even out the relatively irregular surface.

To measure hardness accurately it is also important that the load on the penetrator ball 54 be measured independently of any load on the tubular stop member 60. If the load on both the tubular stop member 60 and the penetration ball 54 are concurrently measured and totaled via one load measuring device, friction forces between various relatively moving portions of the overall system could significantly contribute to substantial measuring errors. It is likewise important, therefore, that the penetrator ball 54 and penetrator rod 50 be vertically movable independently of each other. It is important to note that the load exerted on the hub 30a of the load cell 22 by the penetrator rod 50 is substantially independent of the load exerted on the load cell 24 by the tubular stop 60. The load exerted on the penetrator rod 50 is equal to the load exerted by the penetrator ball 54 on the workpiece W and thus an accurate indication of hardness of the workpiece W. As will be described hereinafter, the loads exerted on the penetrator rod 50 and the tubular stop member 60 are individually measured.

When the tubular stop end surface 70 of the stop 60 does not bear against a workpiece W, as illustrated in FIG. 2, the lowermost penetrating surface position 54a of the penetrator ball 54 is disposed at a level below the end surface 70 by a distance D which is substantially greater than either of the gaps g and g1 so that the penetrator ball 54 may be used to penetrate the specimen W to a depth H (FIG. 3A) which is more than 50% of the ball diameter when the gaps g and g1 are closed. Generally, if the penetrator ball 54 is inserted into the workpiece W to a depth H which is equal to one-half the ball diameter the penetration is sufficiently below the outer surface of the specimen so that consistent readings may be obtained substantially unaffected by skin effect. Even though the overall penetration of the tubular stop member 60 will be greater if the specimen W has a relatively thick soft skin layer s, the effective penetration into the underlying material will be the same as for a specimen with a thin skin layer s.

As previously mentioned, for reliable, consistent, and accurate measurements, it is important that the penetrating ball 54 always be inserted into the specimens W to the same penetration depth H. When the penetrator ball 54 enters a specimen W a predetermined depth the lower end surface 70 of the tubular stop member 60 will engage the workpiece W and prevent further penetration of the penetrator ball 54 into the workpiece with the exception of any deformation T (FIG. 3A) of the relatively soft and uneven workpiece skin layer s, and any deformation of the load cell web 34. The lower end 70 of the stop is chamfered to reduce the surface area of the tubular stop member 60 which engages the surface so that in the event that a rough casting W includes large surface irregularities, as illustrated at L, the stop 60 may pass therebetween. The stop end surface 70 must have sufficient area that the tubular stop member 60 will not penetrate the workpiece W beyond the relatively soft skin material s to a depth T. The end surface 70 of the tubular stop member 60 will tend to iron out any minor irregularities in the relatively soft skin material s of the "as is" casting immediately surrounding the penetrator rod 50 so that the ball 54 will penetrate to substantially the same distance to obtain consistent measurements on specimens having irregular surfaces. As will be immediately described, when the penetrating ball 54 has entered the workpiece W and the end surface 70 of the stop 60 has slightly compacted the outer soft skin s, further penetration of the ball 54 in the workpiece will be positively interrupted by the tubular stop member 60.

Figure 6:
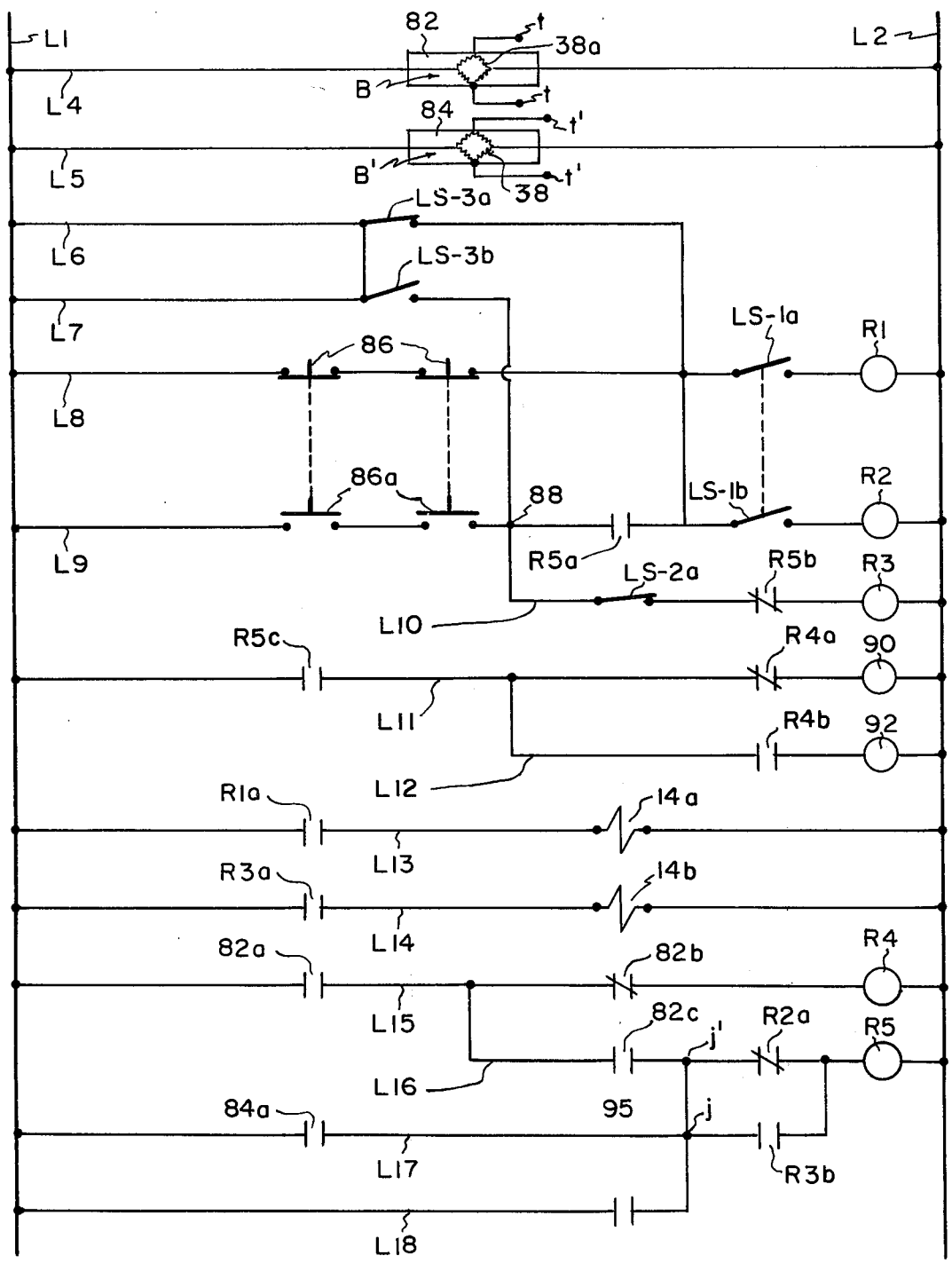
FIG. 6 is a schematic diagram of an electrical control circuit incorporated in the present invention.

Turning now more particularly to FIG. 6, a control circuit is illustrated and includes a pair of circuit lines L1 and L2 connected to suitable source of power such as 110 volt, 60 cycle, alternating current. A series of circuit and sub-circuit lines L4 through L18 are connected across the lines L1 and L2. Connected in line L4 is a hardness comparator and hardness meter, generally designated in block form at 82, for measuring the load on the penetrator rod 50 and includes a strain gauge resistor 38a connected in a bridge circuit B. When the rib 34a is deformed by the penetrator rod 50, the resistance of the strain gauge resistor 38a will change to unbalance the bridge circuit B which provides an output voltage at terminals t that is compared with a predetermined voltage to determine relative hardness. The hardness tester 82 includes normally open contacts 82a (line L15) which close if the hardness of the specimen is within a predetermined range. The hardness tester 82 also includes a set of normally closed contacts 82b (line L15) and a set of contacts 82c (line L16) which open and close, respectively, if the hardness of the material being tested is out of an acceptable range to end the test as will be described more fully hereinafter. The tester portion of the tester and comparator device 82 may suitably comprise the type sold by Electronics Research Corporation (ERC), P. O. Box 913, Shawnee, Kan., as Model 3010 B1000. The comparator portion of the device 82 may suitably comprise a dual channel, bi-directional, tracking comparator of the type sold by ERC as Model A2443.

Connected in line L5 is stop meter and comparator apparatus 84 which includes the strain gauge resistor, schematically designated 38 connected in a normally balanced bridge circuit B'. The resistance of the strain gauge resistor 38 is dependent upon the deflection of the rib 34 to change the balance of the bridge circuit B'. When the bridge circuit B' is sufficiently unbalanced, the output voltage at terminals t' will reach a predetermined level to close a set of normally open contacts 84a (line L17) when the tubular stop member 60 engages the workpiece W with a predetermined force. If, for example, the skin s of the workpiece is very soft, when the stop first engages the material, the contacts 84a will not close until the end surface 70 is sufficiently well seated against the underlying material to be tested. The stop meter and comparator apparatus 84 is identical to the apparatus 82 (line L4).

Figure 1:
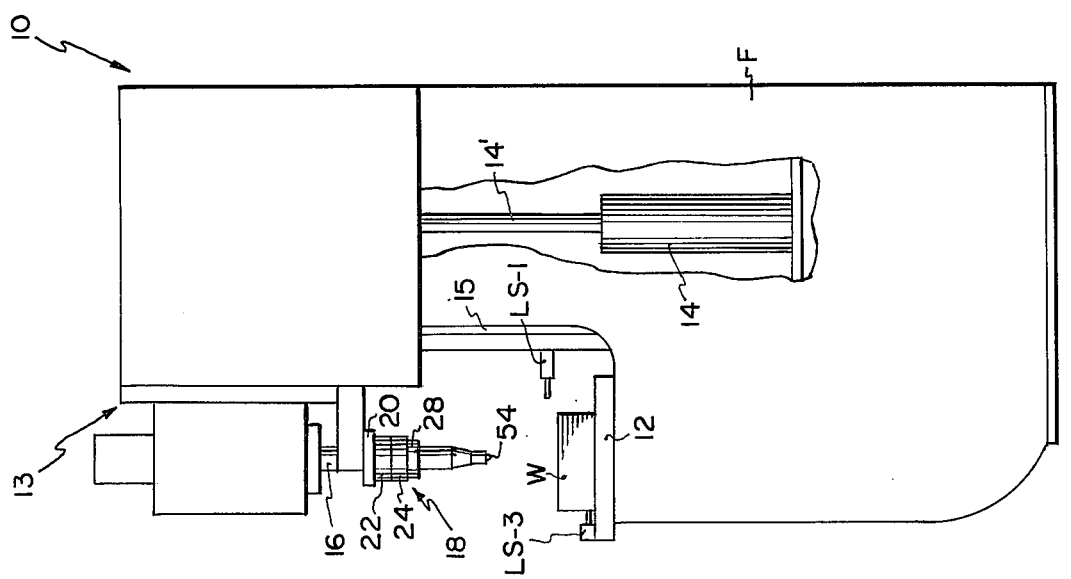
FIG. 1 is a side elevational view of a compacting machine or press in which apparatus constructed according to the present invention is incorporated.

The line L6 is connected to line L1 and includes a set of normally closed contacts LS-3a, which are opened when the limit switch LS-3 (FIG. 1) is actuated by a casting or workpiece W being moved into position on the work table 12. Connected across the lines L1 and L2 is a line L8 including a pair of normally closed, palm-actuated contacts 86 and the normally open contacts LS-1a which are closed when the support rod 16 is lowered from the position illustrated in FIG. 1 to the position illustrated in FIG. 3 to trip the limit switch LS-1. Also connected in line L8 is a press opening relay R1, including a set of normally open contacts R1a (line L13) which close when the relay R1 is energized. Line L9 is connected across the lines L1 and L2 and includes a set of normally open, palm-actuated, pushbutton contacts 86a which are ganged to the palm-operated contacts 86 and are closed when the contacts 86 are open. Also connected in line L9 are a set of contacts R5a which close when a lock stop relay R5 (line L16) is energized. The contacts R5a are connected to a set of normally closed limit switch contacts LS-1b, which open when the switch LS-1 is tripped, and a reset relay R2, including a set of normally open contacts R2a (line L17) which are closed when the relay R2 is energized.

A set of normally open limit switch contacts LS-3b is connected in line L7 between the line L1 and a junction 88 (line L9) between the contacts R5a and the palm-actuated button contacts 86a (line L9). Circuit line L10 is connected between the junction 88 and the line L2 and includes a set of normally closed relay operated contacts R5b, which open when a "lock-stop" relay R5 (line L17) is energized, and a relay R3. The relay R3, when energized, is operative to close sets of contacts R3a (line L14) and R3b (line L17).

Circuit line L11 is connected across lines L1 and L2 and includes a set of normally open contacts R5c, which close when the lock-stop relay R5 (line L16) is energized, and a set or normally closed relay contacts R4a, which open when a "reject-accept" relay R4 (line L15) is energized, and a reject indicator lamp 90. Connected in circuit line L12, across the contacts R4a and indicator 90, is a set of normally open contacts R4b which close when the reject-accept relay R4 (line L15) is energized and an "accept" indicator lamp 92. Circuit line L13 is connected across the lines L1 and L2 and includes the normally open contacts R1a and a solenoid 14a which, when energized, directs operating fluid to the carriage lowering cylinder 14 in a direction so as to move the piston rod 14' and carriage 13 downwardly. Circuit line L14 is connected across the lines L1 and L2 and includes normally open relay contacts R3a, and a carriage raising solenoid 14b which, when energized, directs operating fluid to the cylinder 14 in a direction so as to move the piston rod 14' and carriage 13 upwardly. Circuit line L15 is connected across the lines L1 and L2 and includes the normally open hardness meter contacts 82a, the normally closed hardness meter contacts 82b, and the hardness accept-reject relay R4. Energization of relay R4 occurs if the specimen tested is at an acceptable hardness level. Circuit line L16 is connected between the junction of the contacts 82a and 82b and the line L2 and includes the set of hardness meter contacts 82c, the normally closed relay contacts R2a, which open when the reset relay R2 is energized, and the lock-stop relay R5 which, when energized, stops movement of the penetrator ball 54 toward the workpiece W. Connected in line L17, between the line L1 and the relay R5, are the normally open "stop meter" contacts 84a and the normally closed relay contacts R3b. A line 95 connects the junction of contacts R3b and the contacts 84a (line L17) and the junction j' of the contacts R2a and 82c (line L16) contacts R2a. The circuit line L18 is connected between the line L1 and the junction j and includes a set of relay operated, holding contacts R5b which close when the lock stop relay R5 (line L16) is energized.

THE OPERATION

Figure 4:
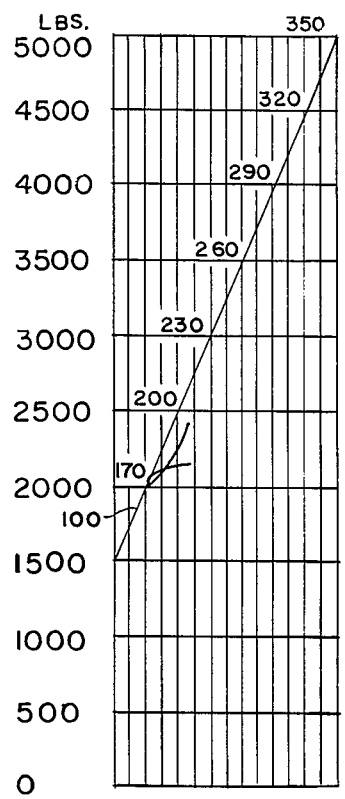
FIGS. 4 and 5 are diagrams graphically illustrating the loads on the various elements throughout a typical test.
Figure 5:
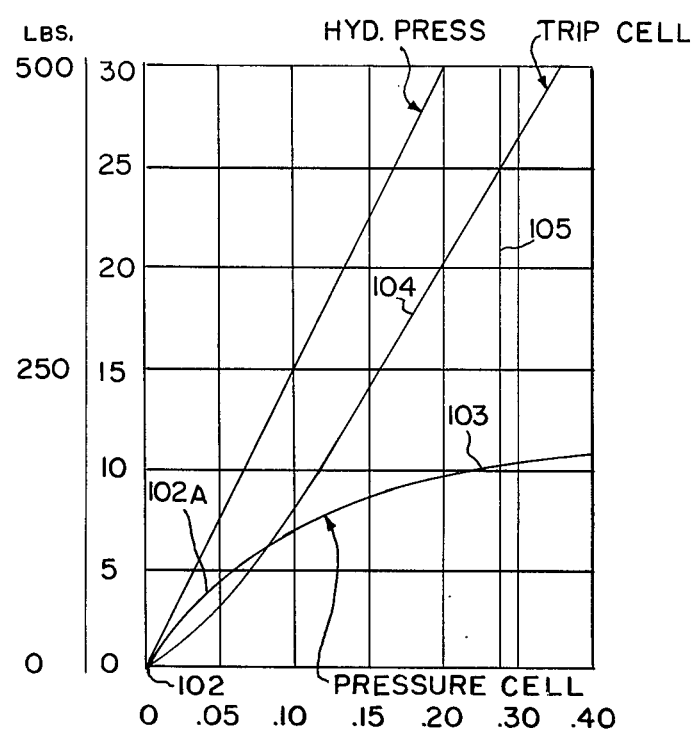

The initial condition of the circuit is such that the relays R1, R3, R4 and R5 are released and the relay R2 is made. The limit switches LS-2 and LS-3 are released and the limit switch LS-1 is made or tripped so that the elements of the circuit are in the positions illustrated in FIG. 6. A specimen W is then positioned on the work table 12 to make or trip limit switch LS-3 and open the switch contact LS-3c (line L6) and close the limit switch contacts LS-3b (line L7). When the contacts LS-3b (line L7) close, the relay R3 (line L10) is energized to close the contacts R3a (line L14) to energize the carriage lowering solenoid 14b which causes the carriage 13 and the testing apparatus 18 to be lowered. As the penetrator ball 54 penetrates the workpiece W, the web 34a on the load cell 22 will deflect and the resistance of the strain gauge resistor 38a will continue to change as the force or load exerted on the web 34a continues to rise. As indicated at 100 in FIGS. 4 and 5, for example, the load on the penetrating rod 50 increases substantially linearly until the stop 60 engages the workpiece, indicated at 102 (FIGS. 4 and 5). The load on the penetrating rod 50 starts to decrease (see 103 - FIG. 5) as the stop 60 assumes part of the load (see 104 - FIG. 5) as it engages the workpiece W and penetrates or compacts the relatively soft and uneven skin material s to a depth T. When the reaction force of the material equals the compacting force of the stop 60 and the stop 60 "bottoms out", the ball 54 will have penetrated the specimen W to a depth H. If the load on the penetrator rod 50 is within an acceptable range, the hardness comparator 82 will then close the contacts 82a (line L15) to energize the accept-reject relay R4, indicating an acceptable hardness. This opens the contacts R4a (line L11) and closes the contacts R4b (line L12). The indicator light 92, indicating acceptance, is not energized at this time however, because the contacts R5c (line L11) remain open.

It should be noted that as the penetrator ball 54 bears against a workpiece, it and the penetrator rod 50 are moved upwardly, relative to the stop 60, to close the gap $g2$ and create a gap $g3$ at the lower and thereof between the shoulder 58 (FIG. 3A) and the beveled flange 56. When the load on the stop 60 reaches a predetermined level (as indicated at 105 in FIG. 5), the stop meter and comparator 84 (line L5) will close the contacts 84a (line L17) and cause the lock stop relay R5 (line L17) to be energized. The contacts R5c (line L11) close to trigger the light 92 indicating acceptable workpiece. Thus, the system does not function to indicate an acceptable hardness until the load exerted on the stop 60 has reached a predetermined level. The indicator 92, of course, can provide a digital readout so that the hardness can be permanently recorded. The penetrator rod 50 is received in the stop 60 with an "air clearance" fit. When the lower penetrator rod end 56 is raised off the stop shoulder 58 this substantially eliminates any side loading by the stop 60 on the penetrator rod 50.

If the hardness of the workpiece W is above a predetermined level, i.e., too hard, the hardness device 82 opens the contacts 82b and closes the contacts 82c which immediately energizes the lock stop relay R5 prior to the stop 60 reaching its lowermost position. This closes the contacts R5a (line L9) and completes the circuit through the contacts LS-1a (line L8) to the relay R1 (line L8) when the palm-actuated switches 86 (line L8) are released. This closes the contacts R1a (line L13) to energize the carriage retract solenoid 14a and withdraw the test apparatus 18. The energization of relay R5 also causes the relay contacts R5b (line L10) to open to release the relay R3 (line L10). This feature accelerates testing of workpieces which turn out to be unacceptable.

When the palm-actuated contacts 86 and 86a are again tripped, the cycle will be repeated.

THE ALTERNATE EMBODIMENT

Figure 7:
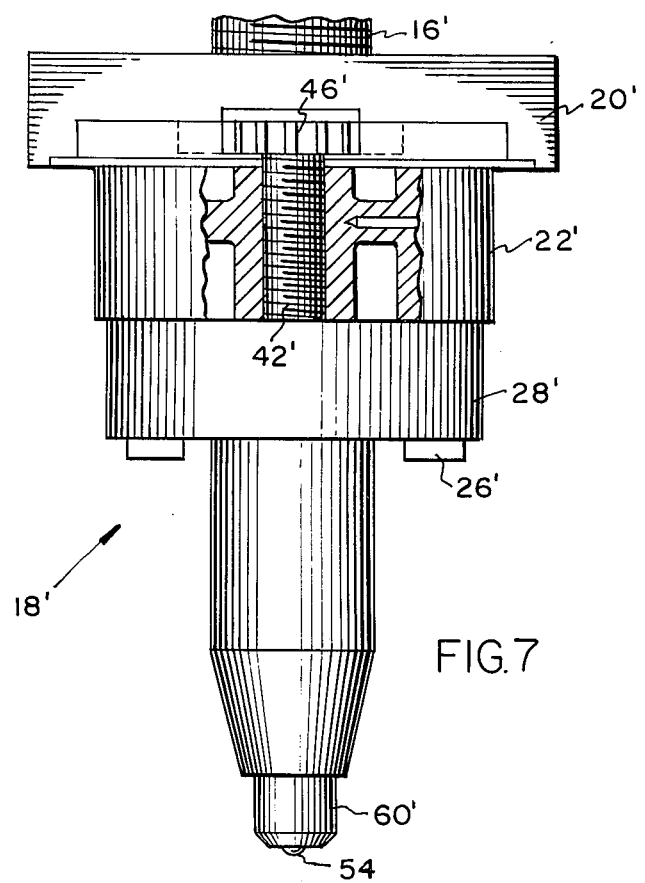
FIG. 7 is a slightly modified embodiment.

The apparatus illustrated in FIG. 7 is generally similar to the apparatus illustrated in FIG. 2, and identical components are identified with idential characters followed by a prime designation. The apparatus illustrated in FIG. 7 differs from the apparatus illustrated in FIG. 2 only in that the load cell 24 has been eliminated. In the operation of the apparatus illustrated in FIG. 4, the piston 16' is lowered and the stop 60 bears against the specimen W to overcome the force of the cylinder 14 and interrupts the movement of the testing apparatus 18'. The structure also differs in that stop 60 is fixed to and does not extend through, the guide holder 28. The rod 50 is free to move as previously described.

It is to be understood that the drawings and descriptive matter are in all cases to be interpreted as merely illustrative of the principles of the invention, rather than as limiting the same in any way, since it is comtemplated that various changes may be made in various elements to achieve like results without departing from the spirit of the invention or the scope of the appended claims.

What is claimed is:

1. Hardness testing apparatus comprising:
   workpiece penetrating means for penetrating a workpiece to be tested;
   means mounting said workpiece and said penetrating means for relative movement between spread positions and engaged positions in which said penetrating means penetrates said workpiece;
   load bearing stop means engageable with said workpiece for positively physically interrupting said relative movement of said penetrating means and said workpiece after said penetrating means has penetrated said workpiece to a predetermined depth by transmitting any additional force which tends to move said workpiece and penetrating means together directly to said workpiece via said stop means; and
   means for determining the load exerted on said penetrating means by said workpiece independently of any load exerted by said workpiece on said stop means when said penetrating means is at said pedetermined depth.

2. The hardness testing apparatus as set forth in claim 1 including means independent of said determining means for measuring the load exerted on the stop means when said penetrating means is at said predetermined depth, and means responsive to said measuring means for operating said moving means to move said workpiece and said penetrating means to said spread positions.

3. The apparatus as set forth in claim 1 wherein said load determining means comprises a load cell having movable web means, said penetrating means being movable relative to said stop means between a position coupled to said web means for concurrent movement therewith and an uncoupled position in which said penetrating means moves independently of said web means.

4. The apparatus as set forth in claim 1 wherein said penetrating means projects outwardly beyond said stop means in a direction toward said workpiece.

5. The apparatus as set forth in claim 4 wherein said penetrating means is movable independently of said stop means toward and away from said workpiece.

6. The apparatus as set forth in claim 5 wherein said stop means comprises a tubular member slidably receiving at least a portion of said penetrating means.

7. The apparatus as set forth in claim 5 wherein said load determining means comprises a load cell connected thereto including variable electrical resistor means having an electrical resistance value which is dependent upon the load exerted by said penetrating means on said workpiece.

8. The hardness testing apparatus as set forth in claim 1 including: additional load determining means for individually measuring the load exerted on said stop means when said stop means is in engagement with said workpiece; said first mentioned load determining means including means for indicating whether the load exerted on said penetrating means is at a predetermined level; and means connected in circuit with said load determining means for permitting operation of said indicating means only after the load exerted on said stop means is at a predetermined level.

9. The hardness testing apparatus as set forth in claim 8 wherein said first mentioned load determining means and said additional load determining means comprise a pair of stacked load cells having variable electrical resistance elements therein, and first and second reactor means is provided for reacting between said penetrating means and said stop means and portions of said load cells to deform said portion when a load is exerted thereon, one load cell bearing against one of said reactor means and including a passage therein which freely receives the other of said additional reactor means.

10. The hardness testing apparatus as set forth in claim 8 wherein each of said load cells includes a load cell mounting portion and a deformable portion of reduced axial thickness; said stop means comprises aa tubular member adapted to bear axially against the deformable portion of said one load cell when it engages said workpiece, said penetrator means comprises an axial rod received within said tubular member and bearing against the deformable portion of said other load cell.

11. The hardness testing apparatus as set forth in claim 10 including actuable means for axially adjusting the relative axial positions of said tubular member and said penetrating means.

12. The hardness testing apparatus as set forth in claim 10 including holder means clamped to opposite ends of said stack of load cells, one of said holder means including an axial passage slidably receiving said tubular member, said tubular member having a portion, normally axially spaced from said holder means, movable into axial engagement with said one holder means after said tubular member deforms the deformable portion of said other load cell a predetermined amount.

13. The hardness testing apparatus as set forth in claim 12 including an axially extending guide connected to said one holder means and slidably receiving said tubular member.

14. The apparatus as set forth in claim 1 wherein said stop means mounts said penetrating means for movement therewith and for limited, free, reciprocal movement relative thereto.

15. The apparatus as set forth in claim 14 wherein said stop means comprises a tubular member having an outer end surface for engaging and compacting the outer surface portion of said workpiece, said penetrating means comprising an elongate rod internally recieved by said tubular member and having an indenter member normally projecting outwardly beyond said outer end surface a predetermined amount but being movable with said rod relative to said tubualr member in a direction toward said end surface.

16. Hardness testing apparatus comprising:
   workpiece penetrating means for penetrating a workpiece to be tested;
   means for relatively moving a workpiece and said penetrating means between spread positions and engaged positions, in which said penetrating means penetrates said workpiece;
   stop means engageable with said workpiece for positively interrupting said relative movement after said penetrating means has penetrated said workpiece to a predetermine depth;

means for determining the load exerted on the penetrating means when said penetrating means is at said predetermined depth; and additional means for individually determining the load exerted on said stop means when said penetrating means is at said predetermined depth;

said means for relatively moving said workpiece and said workpiece penetrating means operating in response to a predetermined load being exerted on said first mentioned load determining means and a predetermined load exerted on said additional load determining means.

17. Hardness testing apparatus comprising:

workpiece penetrating means for penetrating a workpiece to be tested;

means for relatively moving a workpiece and said penetrating means between spread positions and engaged positions in which said penetrating means penetrates said workpiece;

stop means engageable with said workpiece for positively interrupting said relative movement after said penetrating means has penetrated said workpiece to a predetermined depth; and means for determining the load exerted on the penetrating means when said penetrating means is at said predetermined depth;

said stop means mounting said penetrating means for movement therewith and for limited, free, reciprocal movement relative thereto, said penetrating means being movable relative to said stop means between an outwardly projecting position uncoupled from said load determining means and a less projecting position in which said penetrating means is coupled to said load determining means.

18. The apparatus as set forth in claim 17 including a frame mounting said penetrating means and stop means for independent movement limited relative thereto and to each other, said stop means being movable relative to said frame as said stop means engages said workpiece between a position removed from said frame and a position engaging said frame.

19. Hardness testing apparatus comprising:

workpiece penetrating means for penetrating a workpiece to be tested;

means for relatively moving a workpiece and said penetrating means between spread positions and engaged positions in which said penetrating means penetrates said workpiece;

load bearing stop means engageable with said workpiece and physically reactible between said workpiece and a portion of said penetrating means for positively physically interrupting said relative movement after said penetrating means has penetrated said workpiece to a pre-determined depth; and means for determining the load exerted on said penetrating means by said workpiece independently of any load exerted by said workpiece on said stop means when said penetrating means is at said predetermined depth.

* * * * *